United States Patent [19]

Fujii et al.

[11] 4,096,340

[45] Jun. 20, 1978

[54] PROCESS FOR THE PREPARATION OF DIMETHYL TEREPHTHALATE

[75] Inventors: Takao Fujii; Shinichi Takeda; Satoshi Takahashi; Koshi Namie, all of Matsuyama, Japan

[73] Assignee: Teijin Hercules Chemical Co., Ltd., Tokyo, Japan

[21] Appl. No.: 583,399

[22] Filed: Jun. 3, 1975

[51] Int. Cl.$^2$ .............................................. C07C 69/82
[52] U.S. Cl. ......................................... 560/77; 560/78
[58] Field of Search ....................... 260/475 R; 560/77

[56] References Cited

FOREIGN PATENT DOCUMENTS

| | | | |
|---|---|---|---|
| 2,327,773 | 12/1974 | Germany | 260/475 |
| 2,244,662 | 4/1974 | Germany | 260/475 |
| 73/96539 | 12/1973 | Japan | 260/475 |

*Primary Examiner*—Jane S. Myers
*Attorney, Agent, or Firm*—Wenderoth, Lind & Ponack

[57] ABSTRACT

In the process for preparing dimethyl terephthalate by oxydizing p-xylene and/or methyl p-toluate with molecular oxygen or a molecular oxygen-containing gas in the presence of a heavy metal catalyst, esterifying the resulting oxidation reaction mixture with methanol, followed by submitting the resulting esterification reaction mixture to distillation to separate dimethyl terephthalate and fractions of lower boiling point than dimethyl terephthalate, and thereafter recycling to said oxidation step (A) the distillation residue containing said heavy metal catalyst and/or (B) the extract portion containing said heavy metal catalyst obtained by further extraction treatment of said distillation residue (A), the improvement which comprises contact-treating said distillation residue (A) or said extract portion (B) with methanol prior to recycling same.

8 Claims, No Drawings

PROCESS FOR THE PREPARATION OF DIMETHYL TEREPHTHALATE

This invention relates to an improved process for preparing dimethyl terephthalate. More particularly, the invention relates to a process which comprises oxidizating p-xylene (PX) and/or methyl p-toluate (MPT) with either molecular oxygen or a molecular oxygen-containing gas in the presence of a heavy metal catalyst followed by the methyl esterification of the oxidation product to obtain an esterification reaction mixture, distilling the so obtained reaction mixture to separate dimethyl terephthalate (DMT) and the fractions of boiling points lower than DMT, and thereafter recycling the heavy metal oxidation catalyst contained in the distillation residue to the oxidation step in a high state of activity and reusing same therein.

Dimethyl terephthalate (DMT) is a compound that is valuable as a starting material for the preparation of fiber- and film-forming polyesters and is being produced commercially on a large scale.

While a great number of methods are known for the preparation of DMT, the SD process and the Witten process described below are the two most widely employed commercially.

According to the SD process, PX is oxidized with a molecular oxygen-containing gas in the presence of a heavy metal catalyst and bromine compound as the promoter in a lower fatty acid solvent such as acetic acid to form terephthalic acid (TA), after which the TA is further esterified with methanol to produce DMT. (See, for example, U.S. Pat. No. 2,833,816).

Thus, TA can be prepared by the SD process by a single-stage oxidation of PX, but the bromine compound used as the promoter and the acetic acid used as the solvent are highly corrosive. Hence, the apparatus must necessarily be made of such expensive materials as titanium, and in spite of this the life of the apparatus is short. Furthermore, a large quantity of acetic acid is required to be used as the solvent and, in addition, since TA is insoluble in acetic acid and also is itself non-meltable, slurries and solids nust be handled in the process. Aside from these many drawbacks when considered from the standpoint of its commercial operation, difficulty is experienced in refining the TA.

Another widely practiced process is referred to as the Witten process. In this process the PX is oxidizec with a molecular oxygen-containing gas in the liquid phase in the presence of a heavy metal catalyst to form p-toluic acid (PTA), which is esterified with methanol to form MPT, after which the resulting MPT is oxidized in the liquid phase with a molecular oxygen-containing gas in the presence of a heavy metal catalyst to be converted to monomethyl terephthalate (MMT) followed by esterifying the MMT with methanol to provide DMT. (See, for example, British Pat. No. 727,989.) According to this process, the PX is submitted to four reaction steps: the oxidation (PTA), the esterification (MPT), the oxidation (MMT) and the esterification (DMT). There has also been a suggestion to oxidize a mixture of PX and MPT followed by esterifying the oxidation product. In this latter case, the mixture of PX and MPT is oxiized in the liquid phase with a molecular oxygen-containing gas in the presence of a heavy metal catalyst, following which the resulting oxidation reaction mixture of PTA and MMT is esterified with methanol. DMT is recovered from the thus formed esterification product, and fresh PX is added to the remaining reaction mixture composed chiefly of MPT, which is then again oxidized to form MMT and PTA. (See, for example, British Pat. No. 809,730.)

The DMT-containing esterification reaction mixture obtained by these Witten processes is usally submitted to distillation to separate therefrom DMT as well as components of lower boiling point than DMT, for example, the various intermediate products which are capable of being converted to DMT on re-oxidation and methyl esterification, such as methyl p-toluate, methyl p-formylbenzoate and p-tolualdehyde. On the other hand, the tarry by-product boiling higher than DMT obtained as the distillation residue containing the heavy metal catalyst used in the oxidation reaction has been hitherto recycled as-obtained to the oxidation step without separating the heavy metal catalyst or after concentrating a part thereof. Alternately, the heavy metal catalyst was separated and recovered from the distillation residue and thereafter recycled to the oxidation step. These were the methods employed in the past for re-utilization of the catalyst, etc.

It is however found according to our studies that when, as above described, the distillation residue or that obtained after its concentration or the heavy catalyst separated from the distillation residue by, say, extraction was recycled to the oxidation step without treating it but in its as-obtained state, there was the drawback that, aw compared with the case where a fresh heavy metal catalyst was used, the yield of DMT was low and furthermore the coloration of the oxidation reaction mixture was high to cause difficulty to be experienced in its subsequent purification.

We have now found that when the aforesaid distillation residue or the heavy metal catalyst separated by extraction therefrom is recycled to the oxidation step after having contact-treated same in advance with methanol, there was an enhancement of the yield of DMT as compared with the case where recycling of the distillation residue or the heavy metal catalyst is carried out without such a methanol treatment and, in addition, that the coloration of the oxidation reaction mixture was less and thus that the subsequent purification was facilitated. It was thus found that results about comparable to that where a fresh catalyst has been used could be achieved.

Thus, in the process for preparing dimethyl terephthalate comprising oxidizing p-xylene and/or methyl p-toluate with molecular oxygen or a molecular oxygen-containing gas in the presence of a heavy metal catalyst, esterifying the resulting oxidation reaction mixture with methanol followed by distilling the resulting esterification reaction mixture to separate dimethyl terephthalate and fractions of lower boiling point than dimethyl terephthalate, and thereafter recycling to the aforesaid oxidation step (A) the distillation residue containing said heavy metal catalyst and/or (B) the extract portion containing said heavy metal catalyst obtained by further extraction treatment of said distillation residue (A); there is provided according to this invention an improved process which is characterized by contact-treating said distillation residue (A) or said extract portion (B) with methanol prior to recycling same.

In the improved process of this invention, the oxidation of PX and/or MPT and the esterification of the oxidation reaction mixture as well as the distillation of the esterification reaction mixtue can be carried out by methods which per se are known. For example, these operations can be carried out in accordance with the methods described in British Patent Specifications Nos. 809,730 and 1,313,083, U.S. Pat. No. 2,894,978 and German Laid-Open Application No. 2,311,209.

Either PX or MPT may be used singly as the starting material, but usually it is advantageous as well as convenient to use a mixture of PX and MPT. The PX and MPT are suitably mixed in a ratio of usually between 2 : 1 and 1 : 4 on a weight basis.

Again, the heavy metal catalyst used in the oxidation step is also that known as being used in the Witten process as an oxidation catalyst. For example, one class of the heavy metals or heavy metal compounds such as mentioned in the aforementioned British Patent Specification No. 809,730 or U.S. Pat. No. 2,894,978 can be used singly, or the Co-Mn or Ni-Mn type oxidation catalysts such as mentioned in the British Patent Specification No. 1,313,083 or German Laid-Open Application No. 2,311,209 can be used. The use of the Co-Mn or Ni-Mn type of catalysts is especially to be preferred.

As the heavy metal compounds, those which are insoluble or difficulty soluble in the reaction mixture, not to mention those which are soluble therein, can be used. Examples of such compounds are the various inorganic compounds such as the carbonates, oxides, hydroxides, etc., of cobalt, nickel and manganese. The preferred compounds are the cobalt, nickel and manganese salts of the organic acids, the most preferred being the acetates, benzoates, toluates and naphthenates of cobalt, nickel and manganese, since these are readily available and, in addition, demonstrate good solubility in the reaction mixture.

The oxidation reaction can usually be carried out at a temperature in the range of 140° – 250° C.

The oxidation conditions can be varied over a broad range within the scope of the hereinbefore-mentioned known processes in accordance with the classes of the starting material and catalyst, etc. A preferred method of the present invention wherein the Co-Mn and Ni-Mn types of catalysts are used will now be briefly described. For instance, when using a Co-Mn type catalyst, the oxidation of a mixture of PX and MPT with molecular oxygen or a molecular oxygen-containing gas is suitably carried out at a temperature of 140° – 240° C., and preferably 160°–220° C., in the presence in the reaction system of a catalyst mixture consisting of a Co-metal or a Co-compound and a Mn-metal or an Mn-compound wherein the atomic ratio of Co to Mn is in the range of 99.9:0.1 – 1:99, and preferably 99:1 – 10:90, in such a concentration that the total amount of these metals, calculated as manganese and cobalt metals, is 50 to 1500 ppm, and preferably 80 – 500 ppm, based on the total amount of the reaction mixture. On the other hand, when the oxidation step is carried out using a Ni-Mn type catalyst, the operation is best carried out by oxidizing the mixture of PX and MPT with molecular oxygen or a molecular oxygen-containing gas at a temperature of 160° – 250° C., and particularly 180°–230° C., in the presence of a catalyst mixture consisting of a Ni-metal or a Ni-compound and an Mn-metal or an Mn-compound wherein the atomic ratio of Ni to Mn is 95:5 – 0.5:99.5, and preferably 90:10 – 2:98, in such a concentration that the total amount of these metals, calculated as the nickel and manganese metals, is 20–5000 ppm, and preferably 80–800 ppm, based on the total amount of the reaction mixture.

The methyl esterification of the thus obtained oxidation reaction mixture and the distillation can be carried out in accordance with the hereinbefore-described per se known methods.

The essential features of the present invention resides in the point that the heavy metal catalyst-containing distillation residue (A) that is obtained after the distillation as hereinabove described or the heavy metal catalyst-containing extract portion (B) obtained after further extraction treatment of (A) is contacted with methanol to activate said heavy metal catalyst, after which the reactivated catalyst is recycled to the oxidation step. The present invention is especially suitable for activating the Co, Mn, Co-Mn and Ni-Mn types of oxidation catalysts.

By the term "distillation residue (A)" that is to be contact-treated with methanol in this invention is meant to include the bottom component that remains after separation by distillation substantially all of the crude DMT or a major portion thereof and the fractions of lower boiling point than DMT from the esterification reaction mixture in the so-called Witten process such as herebefore described, or the concentrated product of said bottom component whose concentration has been carried out in the following manner. The distillation residue remaining after separation of DMT and fractions of lower boiling point than DMT are heated at a temperature of, say, 260° – 400° C., and preferably 280°–380° C., and then after recovering the effective components such as DMT that are relatively distilled off with ease, there remains a concentrated product. The method of the present invention can be applied to even such a concentrated product.

Further, in this invention, the heavy metal catalyst-containing extract portion (B) obtained after submitting the distillation residue (A) to an extraction treatment can also be submitted to the contact-treatment with methanol.

In extracting and separating the heavy metal catalyst from the aforesaid distillation residue, an aqueous solvent is conveniently used. As this aqueous solvent, in addition to water, mention can be made of the solvent mixtures of such lower aliphatic alcohols as methanol and water and the solvent mixtures of a lower fatty acid and water. The extraction can be carried out by any of such liquid-liquid extraction systems as batch extraction, concurrent multistage extraction, countercurrent multistage extraction and continuous countercurrent extraction systems. The thus obtained extract can be then submitted in its as-obtained state to the methanol treatment to be hereinafter described or, if necessary, after having removed a part or all of the extraction solvent.

There are imposed no strict restrictions in carrying out the methanol treatment in accordance with the present invention as long as it is carried out in such a manner that an intimate contact is had between the aforesaid distillation residue (A) or the extract portion (B) and the methanol.

For instance, the temperature at which the contact between the distillation (A) or the extract portion (B) and the methanol is made is not critical, and the temperature can be varied within a broad range in accordance with the oxidation, esterification and distillation conditions employed. However, a temperature usually in the range of 100°–450° C., preferably 150°–400° C., and more preferably 170° – 350° C., is suitably used.

If a temperature lower than 100° C. is used, there is not much improvement in the activity of the recovered catalyst, and thus the activation effects ascribable to the methanol treatment is small. On the other hand, when the temperature exceeds 450° C, this also is not desirable. While the activation effects are not affected, there is an increase in the equipment costs due to the increased reaction pressure, a loss of methanol due to the formation of dimethyl ether, etc.

The amount of methanol used in the contact treatment is influenced by the class of the distillation residue (A) or the extract portion (B) and thus cannot be specifically stated. However, the methanol is usually used in an amount of at least 0.02 part by weight for each part by weight of the distillation residue (A) or the extract portion (B). While there is imposed no particular restriction as to the upper limit, the use of the methanol in too large an amount is not economical. Hence, it should not be more than 20 parts by weight. In the case of especially the distillation residue (A) an amount in the range of 0.05-10 parts by weight is preferred. On the other hand, in the case of the extract portion (B), methanol is conveniently used in an amount of at least 0.2 part by weight, and preferably in the range of 0.5-1000 parts by weight.

While the length of time the distillation residue (A) or the extract portion (B) is contacted with methanol in this invention can be suitably chosen in accordance with such conditions as the contact temperature, etc., usually 0.1 - 20 hours should be suficient. If the contact time is too short, the effects that are to be had by the contact with the methanol is insufficient. On the other hand, if the time is too long, this also is not desirable, for not only is it uneconomical, but also loss of the methanol due to side reactions takes place.

The procedure to be employed in this invention for effecting the contact of the distillation residue (A) or the extract portion (B) with the methanol includes no particular restrictions. However, advantageously employed is such a procedure as, for example, that of carrying out the contact by the batch method consisting of charging the distillation residue (A) or the extract portion (B) and the methanol to a closed pressure vessel and stirring the contents with heating, or that of carrying out the continuous countercurrent contact of the liquid distillation residue (A) or the extract portion (B) with a gaseous methanol, using a tray column, bubble-cap column or a packed column.

The distillation residue (A) or the extract portion (B) that has thus been treated with the methanol can be recycled directly to the oxidation step, but in the case of the methanol-treated distillation residue (A), it can, if necessary, be submitted to a heavy metal catalyst extraction treatment, as hereinbefore described, after which the resulting heavy metal catalyst-containing extract portion or the extract residue remaining after removing a part or all of the extraction solvent can be recycled to the oxidation step.

On the other hand, the methanol that is present after its contact with the distillation residue (A) or the extract portion (B) may or may not be removed prior to recycling the residue (A) or the extract portion (B).

Thus, there are had various excellent technical advantages by recyclng the methanol-treated distillation residue (A) or extract portion (B) to the oxidation step in accordance with the invention process. Not only is it possible to achieve a marked improvement in the yield of DMT over the conventional processes, but also the degree of coloration of the oxidation reaction mixture obtained from the oxidation step is much less, with the consequence that the purification of the DMT is facilitated in the subsequent step.

The following examples are given for more fully illustrating the present invention, it being understood that these examples are merely given for faciliating an understanding of the invention and are not to be construed as limiting the invention thereto.

EXAMPLES 1 and 2

A mixture of PX and MPT in a weight ratio of 1:1.4 was oxidized in the liquid phase with air continuously for a residence time of 4.5 hours at 165° C. and under a pressure of 3.9 Kg/cm$^2$ gauge in the presence of cobalt acetate and manganese acetate to obtain an oxidation product consisting predominantly of PTA and MMT.

This was followed by esterifying the so obtained oxidation product with methanol to obtain an ester mixture consisting predominantly of MPT and DMT.

This ester mixture was submitted to continuous distillation under a column top pressure of 110 mm Hg and at a column bottom temperature of 240° C. to separate DMT and a product of lower boiling point than DMT.

Five hundred grams of this distillation residue (A) and 125 grams of methanol were charged to a 1000-cc stainless steel autoclave equipped with a stirrer. After purging the inside of the actoclave with nitrogen, the contact of the residue (A) with the methanol was carried out for the periods of time and temperatures shown in Table 1 with stirring. After the methanol treatment, the mixture was withdrawn in toto, and the methanol was removed by evaporation. Four hundred grams of the resulting methanol-treated residue (B) and 400 grams of water were charged to a 3-necked flask and stirred for 2 hours at 90° C. After completion of the extraction, the two layers were separated, and a pink water layer was obtained. On evaporation of this water layer to dryness, a recovered catalyst containing cobalt and manganese in the amounts shown in Table 1 was obtained.

The oxidation reaction was then carried out using this recovered catalyst. A stainless steel 500-cc autoclave fitted with a reflux condenser, a stirrer and a gas introducing inlet was charged with 60 grams of PX, 140 grams of MPT, 5 grams of PTA and the aforesaid recovered catalyst in an amount such that its Co concentration, calculated as metallic Co, would be 0.01 weight % % of the liquid chemicals charged. The reaction was then carried out for 3.5 hours at a reaction temperature of 165° C. and a pressure of 10 Kg/cm$^2$ gauge with high-speed agitation by blowing in air such that the flow rate thereof at the outlet would be 1500 cc/min. After completion of the reaction, the reaction product was cooled and withdrawn. Its acid value was determined, and this was used as the measure of the conversion. Further, the yields of the various components were determined by an analysis of its composition. And the yields of DMT and the various effective components, i.e., the intermediates for obtaining DMT (the compounds that can be transformed to DMT by oxidation and esterification, such as PTA, MMT, TA, p-methylbenzyl alcohol, p-tolualdehyde, methyl p-formylbenzoate and p-formyl benzoic acid) were calculated as follows:

Yield of Effective Components (mol%)

-continued $$= \frac{\text{Effective Components Formed (mol)}}{\{\text{PX (mol)} + \text{MPT (mol)}\} \text{ Consumed}} \times 100$$

Further, for comparing the amounts of coloring impurities, 1.0 gram of the oxidation product was dissolved in 45 cc of dimethylformamide and placed in a color comparison tube, and its Hazen Number was determined.

These results are shown conjointly in Table 1.

On the other hand, by way of comparison, a distillation residue not given the aforementioned methanol treatment was similarly submitted to the catalyst extraction treatment to obtain a recovered catalyst, which likewise was used to carry out the same oxidation experiment. The results obtained in this case are shown in Table 1 as results of Control 1.

Again, by way of reference, a similar oxidation experiment was carried out using as catalyst fresh cobalt acetate and manganese acetate. The results obtained in this case are shown in Table 1 as results of Reference Experiment 1.

As control, the heavy metal catalyst was recovered by carrying out the extraction thereof from the distillation residue (A') by operating exactly as in Example 1 but without submitting the distillation residue (A') to a metanol treatment. These extracted and recovered catalysts were treated as in Example 1 to obtain the recovered catalyst. The content of cobalt and manganese in these catalysts are shown in Table 2, below.

These recovered catalysts were used, and the oxidation reactions were carried out as in Example 1. The yields of the effective components, the degrees of coloration of acid values were also determined as in Example 1. The results obtained are shown in Table 2.

Table 2

| | Methanol Treatment Temperature (° C) | Methanol Treatment Time (hr) | Ditillation Residue/ Methanol weight ratio | Metal Content of Recovered catalyst | | Amount of Catalyst used in the Oxidation | | Acid Value of the Oxidation Reaction Product (mgKOH/g) | Yield of Effective Components (%) | Degree of Coloration (Hazen Number) |
|---|---|---|---|---|---|---|---|---|---|---|
| | | | | Co(%) | Mn(%) | Co(mg) | Mn(mg) | | | |
| Example 3 | 270 | 8.0 | 1/1 | 7.0 | 0.14 | 20.6 | 0.41 | 243 | 89.9 | 90 |
| Control 2 | — | — | — | 13.57 | 0.30 | 20.5 | 0.45 | 116 | 78.6 | 400 |

EXAMPLE 4

A distillation residue (A') was obtained by operating in the same manner as in Example 3. This distillation residue contained 0.0865% by weight of cobalt and 0.0018% by weight of manganese as the heavy metal catalyst. Three hundred grams of this distillation residue (A') and 150 grams of methanol were contracted for 2 hours at 260° C. as in Example 1 to obtain a treated Table 1

| Experiment No. | Methanol Treatment Temperature (° C) | Methanol Treatment Time (hr) | Metal Content of Recovered catalyst | | Amount of Catalyst used in the Oxidation | | Acid Value of the Oxidation Reaction Product (mgKOH/g) | Yield of Effective Components (%) | Degree of Coloration (Hazen Number) |
|---|---|---|---|---|---|---|---|---|---|
| | | | Co(%) | Mn(%) | Ca(mg) | Mn(mg) | | | |
| Example 1 | 200 | 0.5 | 5.4 | 0.11 | 20.5 | 0.42 | 314 | 92.6 | 60 |
| Example 2 | 280 | 0.5 | 3.6 | 0.076 | 20.5 | 0.43 | 307 | 92.3 | 50 |
| Control 1 | — | — | 9.7 | 0.234 | 20.5 | 0.49 | 209 | 84.4 | 250 |
| Reference Experiment 1 | — | — | — | — | 20.5 | 0.45 | 313 | 92.7 | 50 |

EXAMPLE 3

As the distillation residue (A) obtained in Example still contains some DMT, it was further submitted to continuous distillation at a column top pressure of 35 mm Hg and a column bottom temperature of 270° C. to recover such components as DMT to thus obtain a distillation residue (A').

The methanol treatment of this distillation residue (A') was carried out for 8 hours at 270° C. by operating as in Example 1, using 300 grams of the distillation residue (A') and 300 grams of methanol. After the methanol treatment, the treated residue (B') and water were charged to a 3-necked flask in a proportion of 2 parts by weight of the former to one part by weight of the latter, after which the extraction was carried out by operating as in Example 1 to recover the heavy metal catalyst.

residue (B').

The oxidation reaction was carried out using the so obtained treated residue (B'). That is, an autoclave of same type as used in Example 1 was charged with 60 grams of p-xylene, 140 grams of p-methyl toluate, 5 grams of p-toluic acid and 27 grams of the treated residue (B'), and the oxidation reaction was carried out under identical conditions as in Example 1. After completion of the oxidation reaction, the acid value of the reaction product and its degree of coloration were determined as in Example 1. The acid value was 247 mg KOH/g, and the degree of coloration was 150.

When, as control, the oxidation reaction was carried out exactly in the same manner as described above but using the distillation residue (A') directly as the oxidation catalyst without treating it with methanol, the oxidation reaction ceased in 20 minutes, and a satisfactory reaction product could not be obtained.

nese acetate and nickel acetate as catalysts (Reference Experiment 2).

Table 3

| Experiment No. | Methanol Treatment Temperature (° C) | Methanol Treatment Time (hr) | Amount of Catalyst used in the Oxidation | | Acid Value of the Oxidation Reaction Product (mgKOH/g) | Yield of Effective Components (%) | Degree of Coloration (Hagen Number) |
|---|---|---|---|---|---|---|---|
| | | | Mn(mg) | Ni(mg) | | | |
| Example 5 | 250 | 0.5 | 20.4 | 20.5 | 273 | 93.7 | 50 |
| Control 3 | — | — | 20.6 | 20.5 | 168 | 82.2 | 350 |
| Reference Experiment 2 | — | — | 20.5 | 20.5 | 273 | 93.8 | 40 |

EXAMPLE 5

A mixture of PX and MPT in a weight ratio of 1:1.3 was oxidized in the liquid phase with air continuously for a residence time of 4 hours at 200° C. and a pressure of 10 Kg/cm$^2$ gauge in the presence of manganese acetate and nickel acetate to obtain an oxidation product consisting predominatly of PTA and MMT.

This was followed by esterifying the so obtained oxidation product with methanol to obtain an ester mixture consisting predominantly of MPT and DMT.

This ester mixture was distilled under a pressure of 110 mm Hg and, after terminating the distillation at a point that no further distillation takes place at a still temperature of 240° C., the DMT and components of lower boiling point than DMT were separated.

This distillation residue was then treated with methanol and extracted as in Examples 1 and 2 to obtain a recovered catalyst.

The oxidation experiment was then carried out using the so obtained recovered catalyst.

An autoclave identical to that used in Examples 1 and 2 was changed with 60 grams of PX, 140 grams of MPT, 5 grams of PTA and the recovered catalyst in an amount such that its Ni concentration would be 0.01% by weight of the liquid chemicals charged. The reaction was then carried out for 2.5 hours at a reaction temperature of 200° C. and pressure of 10 Kg/cm$^2$ gauge with highspeed agitation by blowing in air such that its flow rate at the outlet would be 1500 cc/min.

Analyses and calculations were made as in Examples 1 and 2, and the results obtained are shown in Table 3.

On the other hand, by way of comparison, a similar catalyst extraction operation was carried out on a distillation residue which had not been submitted to the above-described methanol treatment to obtain a recovered catalyst, which was used in carrying out a similar oxidation experiment (Control 4).

Again, by way of reference, the oxidation experiment was carried out in like manner but using fresh manga-

EXAMPLE 6

A mixture of PX and MPT in a weight ratio of 1:1.4 was oxidized in the liquid phase with air continuously for a residence time of 5 hours at 150° C. and a pressure of 3.9 Kg/cm$^2$ gauge in the presence of cobalt acetate to obtain an oxidation product consisting predominately of PTA and MMT.

This oxidation product was submitted to esterification and distillation, followed by a methanol treatment and extraction with water to obtain a recovered catalyst.

The oxidation experiment was then carried out using the so obtained recovered catalyst.

An autoclave of the same type as that used in Examples 1 and 2 was charged with 70 grams of PX, 130 grams of MPT, 5 grams of PTA and the recovered catalyst in an amount such that its Co concentration, based on the liquid chemicals charged, would be 0.03% by weight. The reaction was then carried out for 4.5 hours at a reaction temperature of 160° C. and a pressure of 5 Kg/cm$^2$ gauge with high-speed stirring by blowing in air such that its flow rate at the outlet would be 600 cc/min.

Analyses and calculations were made as in Examples 1 and 2 with the results shown in Table 4.

On the other hand, by way of comparison, a distillation residue not given the above-described methanol treatment was likewise submitted to a catalyst extraction operation to obtain a recovered catalyst, which was then used in carrying out a similar oxidation experiment (Control 4).

Table 4

| Experiment No. | Methanol Treatment Temperature (° C) | Methanol Treatment Time (hr) | Amount of Catalyst used in the Oxidation (Co) (mg) | Acid Value of the Oxidation Reaction Product (mgKOH/g) | Yield of Effective Components (%) | Degree of Coloration (Hazen Number) |
|---|---|---|---|---|---|---|
| Example 6 | 270 | 0.5 | 61.5 | 194 | 88.0 | 70 |
| Control 4 | — | — | 61.5 | 115 | 81.5 | 300 |

EXAMPLES 7

A stainless steel 500-cc autoclave fitted with a stirrer was charged with 2 grams of a recovered catalyst obtained by operating exactly as in Control 1 and 100 grams of methanol. After purging the inside of the autoclave with nitrogen, the methanol treatment of the recovered catalyst was carried out by stirring the contents of the autoclave for one hour at 200° C.

After completion of the methanol treatment, the mixture was withdrawn in toto. The methanol was removed by evaporation, and the catalyst was recovered.

Using the so obtained recovered catalyst, the oxidation experiment was carried out as in Example 1 with the results shown in Table 5.

Table 5

| Experiment No. | Amount of Catalyst used in the Oxidation Co(mg) | Amount of Catalyst used in the Oxidation Mn(mg) | Acid Value of the Oxidation Reaction Product (mgKOH/g) | Yield of Effective Components (%) | Degree of Coloration (Hazen Number) |
|---|---|---|---|---|---|
| Ex. 7 | 20.5 | 0.43 | 311 | 92.4 | 60 |
| Control 1 | 20.5 | 0.49 | 209 | 84.4 | 250 |

We claim:

1. The process for preparing dimethyl terephthalate which comprises the steps of:
   (a) oxidizing p-xylene and/or methyl p-toluate with molecular oxygen or a molecular oxygen-containing gas in the presence of a heavy metal catalyst;
   (b) esterifying the resulting oxidation reaction mixture with methanol;
   (c) subjecting the resulting esterification reaction mixture to distillation to separate dimethyl terephthalate and fractions having boiling points lower than that of dimethyl terephthalate, leaving a distillation residue (A);
   (d)
      (i) contacting said distillation residue (A) with at least 0.02 part by weight per part by weight of said distillation residue (A) of methanol at a temperature of 100° to 450° C. and then subjecting it to a heavy metal catalyst extraction treatment to obtain the extract portion (C) containing said heavy metal catalyst, or
      (ii) subjecting said distillation residue (A) to a heavy metal catalyst extraction treatment to obtain an extract portion (B) and then contacting the extract portion (B) with at least 0.02 part by weight per part by weight of said extract portion (B) of methanol at a temperature of 100° to 450° C; and thereafter,
   (e) recycling the thus contacted extract portion (B), or the extract portion (C) to said oxidation step (a).

2. The process of claim 1 wherein said contact-treatment with methanol is carried out at a temperature of 150° – 400° C.

3. The process of claim 1 wherein said contact-treatment is carried out using methanol in an amount of 0.05 – 10 parts by weight for each part by weight of said distillation residue (A).

4. The process of claim 1 wherein said contact-treatment is carried out using methanol in an amount of 0.5–1000 parts by weight for each part by weight of said extract portion (B).

5. The process of claim 1 which comprises using a mixture of p-xylene and methyl p-toluate as the starting material.

6. The process of claim 1 wherein the weight ratio of p-xylene to methyl p-toluate of said mixture ranges from 2:1 to 1:4.

7. The process of claim 1 wherein said heavy metal catalyst is a catalyst of the Co-Mn or Ni-Mn type.

8. The process of claim 1 wherein said oxidation reaction is carried out at a temperature in the range of 140°–250° C.

* * * * *